(12) United States Patent
Tabuchi et al.

(10) Patent No.: US 7,708,870 B2
(45) Date of Patent: May 4, 2010

(54) METHOD OF ELECTROPHORESING PROTEIN

(75) Inventors: Mari Tabuchi, Tokushima (JP); Yoshinobu Baba, Tokushima (JP)

(73) Assignee: Japan Science and Tecnology Agency, Saitama (JP)

( * ) Notice: Subject to any disclaimer, the term of this patent is extended or adjusted under 35 U.S.C. 154(b) by 1037 days.

(21) Appl. No.: 10/500,075

(22) PCT Filed: Dec. 25, 2002

(86) PCT No.: PCT/JP02/13491

§ 371 (c)(1), (2), (4) Date: Jun. 25, 2004

(87) PCT Pub. No.: WO03/058229

PCT Pub. Date: Jul. 17, 2003

(65) Prior Publication Data

US 2005/0016850 A1    Jan. 27, 2005

(30) Foreign Application Priority Data

Dec. 28, 2001    (JP) .............................. 2001-400640

(51) Int. Cl.
*G01N 27/447*    (2006.01)
(52) U.S. Cl. ...................... 204/450; 204/600
(58) Field of Classification Search ................. 204/450; 530/415
See application file for complete search history.

(56) References Cited

U.S. PATENT DOCUMENTS 3,901,870 A * 8/1975 Haupt et al. ............... 530/392

| | | |
|---|---|---|
| 5,173,164 A | 12/1992 | Egen et al. |
| 5,693,291 A | 12/1997 | Strobel et al. |
| 6,187,549 B1 | 2/2001 | Schmidt et al. |
| 2002/0155455 A1* | 10/2002 | Tadayoni-Rebek et al. ..... 435/6 |

FOREIGN PATENT DOCUMENTS

| | | |
|---|---|---|
| CN | 1168176 A | 12/1997 |
| EP | 0 475 555 A1 | 3/1992 |
| JP | 6-230002 A | 8/1994 |
| WO | WO 99/66325 A | 12/1999 |
| WO | WO 02/097421 A1 | 12/2002 |

OTHER PUBLICATIONS

Gordon, MJ, et al. "Protocol for Resolving Protein Mixtures in Capillary Zone Electrophoresis", Analytical Chemistry, vol. 63, No. 1, Jan. 1, 1991, pp. 69-72.*

Li Cheng-Wen et al., Institute of Microbiology and Epidemiology, Academy of Military Sciences, China Academic Journal Electronic Publishing House, pp. 325-330, Dec. 31, 1985.

(Continued)

*Primary Examiner*—Nam X Nguyen
*Assistant Examiner*—J. Christopher Ball
(74) *Attorney, Agent, or Firm*—Birch, Stewart, Kolasch & Birch LLP

(57) ABSTRACT

To provide an electrophoresis method being capable of rapidly analyzing a protein in a native state without carrying out a heat-denaturing pretreatment step, and having even higher sensitivity. The electrophoresis method of the present invention is useful for proteosome analysis and medical diagnosis.

6 Claims, 16 Drawing Sheets

OTHER PUBLICATIONS

Edited by Japanese Electrophoresis Society, "Saishin Denki Eido Jikkenho", Ishiyaku Pub., Inc., Feb. 25, 1999, pp. 54 to 60.

Edited by Hiroshi Terada, "Tanpakushitsu To Kakusan No Bunri Seisei -Kiso To Jikken-", Kabushiki Kaisha Hirokawa Shoten, Jun. 15, 2001, pp. 66 to 68.

Masaaki Morita, "Shokuhinchu No Tenka Tampakushitsu Bunsekiho No Kento", Norin Suisan Shohi Senta Chosa Kenkyu Hokokusho, Aug. 1996, No. 20, pp. 45 to 54.

Edited by Koichiro Aoki, Hiroshi Nagai, "Saishin Denki Eidoho", Kabushiki Kaisha Hirokawa Shoten, Apr. 1, 1978, pp. 274 to 278.

* cited by examiner

METHOD OF ELECTROPHORESING PROTEIN

This Application is the National Phase under 35 U.S.C.§371 of PCT International Application No. PCT/JP2002/13491 which has an International filing date of Dec. 25, 2002, to which priority is claimed under 35 U.S.C.§371, which claims priority to Japanese Application No. 2001-400640 filed on Dec. 28, 2001, to which priority is claimed under 35 U.S.C.§119.

TECHNICAL FIELD

The present invention relates to a rapid and highly sensitive electrophoresis method of a protein.

BACKGROUND ART

Proteins have been generally subjected to size separation on the basis of SDS-PAGE (polyacrylamide gel electrophoresis) method, and detected. One method of applying this technique to capillary electrophoresis is SDS-CGE (capillary gel electrophoresis), and a method of further applying this method to microchip electrophoresis includes analysis with Agilent 2100 Bioanalyzer (manufactured by Agilent Technologies) using Protein 200 Kit. The proteins have various electric charges in native states, and the positively charged proteins are considered not to migrate in a positive electric field. Therefore, in the above-mentioned conventional method, it is usually necessary to carry out a heat-denaturing treatment of a protein as a pretreatment so that all of the test proteins have negative charges. The heat-denaturing treatment is usually accomplished by heating a protein at 95° to 100° C. for several minutes in a surfactant sodium dodecyl-sulfate (SDS) solution and a reducing agent such as 2-mercaptoethanol or dithiothreitol. 2-Mercaptoethanol or dithiothreitol is used for cleaving S—S bond, and SDS is used for making the electric charges in the entire proteins negative.

Therefore, in the conventional method such as SDS-PAGE method or SDS-CGE method, there is a defect that the time period for this pretreatment step is not shortened, and the procedure is complicated, even though the analyzing step is made rapid by the microchip electrophoresis. Therefore, there has been desired an even more rapid electrophoresis method of a protein. Furthermore, when a biological sample is analyzed, it is necessary to analyze a very small amount of a protein in the sample, so that there has been desired electrophoresis method having even higher sensitivity.

DISCLOSURE OF INVENTION

An object of the present invention is to provide an electrophoresis method being capable of rapidly analyzing a protein in a native state without a heat-denaturing pretreatment step, and having even higher sensitivity.

Specifically, the gist of the present invention relates to:
[1] an electrophoresis method characterized by subjecting a protein to electrophoresis for size separation without a heat-denaturing treatment;
[2] the electrophoresis method according to the above [1], characterized in that a protein dissolved in water is subjected to electrophoresis;
[3] the electrophoresis method according to the above [1] or [2], characterized in that two or more molecular weight markers are subjected to electrophoresis together with a protein, wherein at least one of the markers is adjusted to a lower concentration as compared to a standard concentration;
[4] the electrophoresis method according to any one of the above [1] to [3], characterized in that two or more molecular weight markers are subjected to electrophoresis together with a protein, wherein one of the markers is adjusted to a concentration of 1/10 to 10 times the concentration of a protein to be tested; and
[5] the electrophoresis method according to any one of the above [1] to [4], wherein a type of electrophoresis is selected from the group consisting of capillary electrophoresis method, microchip electrophoresis method and nano-channel electrophoresis method.

BEST MODE FOR CARRYING OUT THE INVENTION

Figure 1:
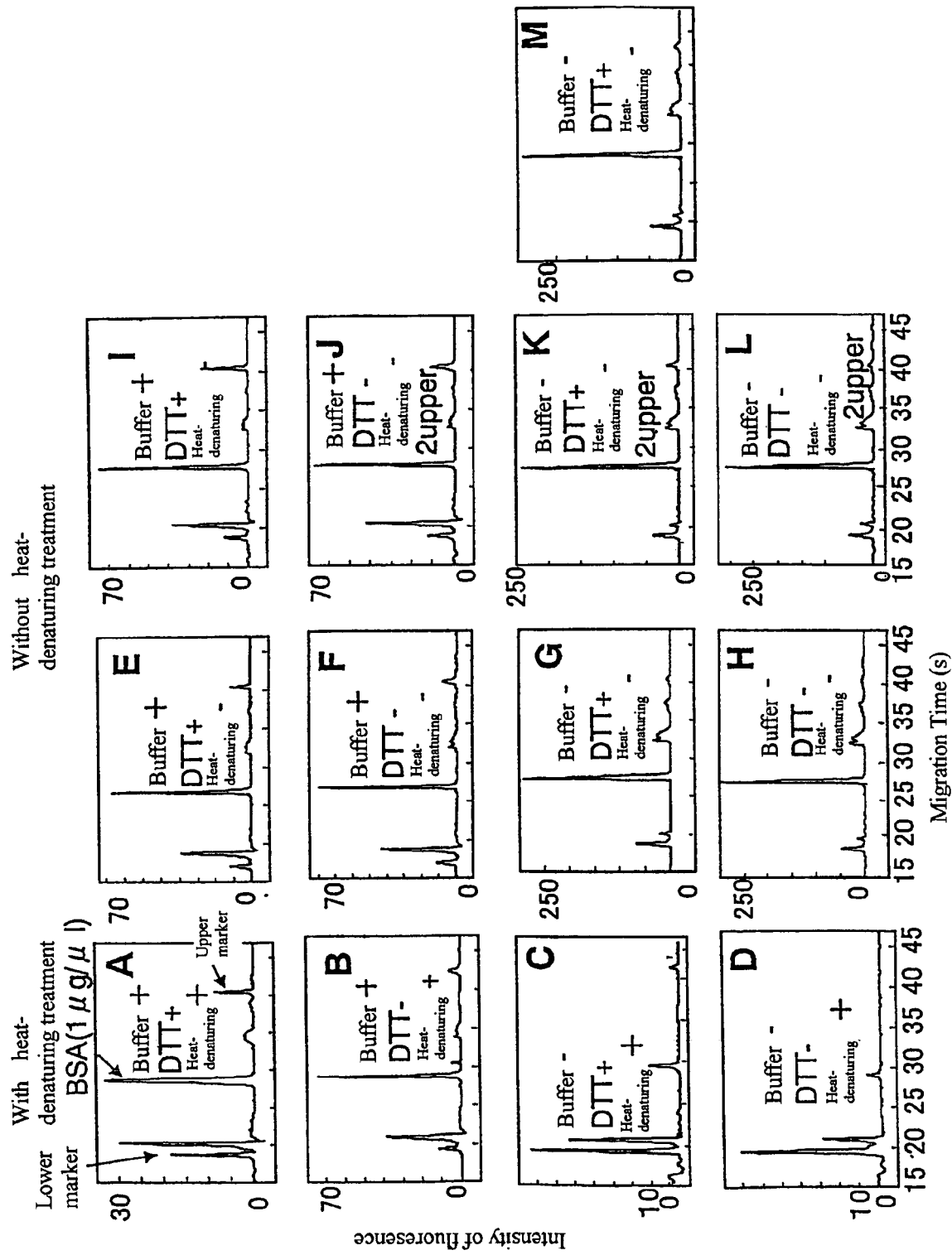
FIG. 1 shows the results for studying electrophoresis conditions in microchip electrophoresis.

One of the significant features of the electrophoresis method of a protein of the present invention resides in that the protein is subjected to electrophoresis for the purpose of size separation without a heat-denaturing treatment. Since the heat-denaturing treatment is not carried out, the electrophoresis method of the present invention has advantages that the analyzing time for electrophoresis can be shortened, and that the procedures can be simplified.

The protein as used herein refers to a compound in which plural amino acids are linked with a peptide bond, and is intended to include naturally derived substances, synthetic substances and short-strand peptides.

The protein which can be analyzed in the electrophoresis method of the present invention includes, but not particularly limited to, naturally derived substances, synthetic substances, and nuclear proteins, glycoproteins, lipoproteins and the like, that contain a constituent other than amino acids. A water-soluble protein is especially preferably used. The determinable molecular size may be such that proteins of all sorts of sizes can be analyzed by appropriately setting a marker, and those proteins having sizes of especially from 6 kDa to 210 kDa can be preferably analyzed. It is preferable that a membrane-bound protein or the like can be applied to the electrophoresis method of the present invention after solubilizing the protein. The solubilization treatment for this purpose can be accomplished by a salt solution or a chelating agent such as EDTA; a mechanical treatment such as ultrasonication; or a treatment with a surfactant or the like.

The carrier for the separation usable in the electrophoresis method of the present invention is not particularly limited, and includes those carriers for separation which can be used for analyzing molecular size separation of a protein in the usual capillary gel electrophoresis, microchip gel electrophoresis or the like, such as polyacrylamide, polyacrylamide gel, hydroxypropyl cellulose, hydroxymethylpropyl cellulose, hydroxyethyl cellulose, methyl cellulose, β-cyclodextrin, α-cyclodextrin and γ-cyclodextrin. Also, cardran, laminaran, marine algae extracts and the like, each containing a β-1,3 glucan structure described in WO 02/097421 are also applicable. The additive for the carrier for the separation includes sodium dodecylsulfate (SDS), Triton X-100, ϵ-aminocaproic acid, 3-[(3-colamidepropyl)-dimethylamino]-1-propane, CHAPS, 6-8 M urea, tetramethylethylenediamine (TEMED), hexyltrimethylammonium bromide (HTAB), dodecyltrimethylammonium bromide (DTAB) and the like.

The buffer for electrophoresis includes Tris-glycine buffer, Tris-borate buffer, Tris-hydrochloric acid buffer, Tris-Tricine buffer, Tris-sodium dihydrogenphosphate buffer, and the like, and buffers which are generally usable as buffers for electrophoresis of a protein. Also, buffers and the like provided in a commercially available kit for electrophoresis of a protein can be used. The above-mentioned buffer for electrophoresis can be used in a concentration that is generally usable as a buffer for electrophoresis of a protein.

The buffer for electrophoresis may contain the above-mentioned carrier for separation. By adding the carrier for separation to the buffer for electrophoresis, the procedures can be simplified, so that the analysis can be more rapidly carried out.

The pH of the buffer for electrophoresis is preferably from 2.0 to 9.0, more preferably from 6.8 to 8.6, from the viewpoints of appropriate electric osmotic flow and preferable electrophoresis of a protein.

As the solution for preparing the sample, an SDS solution, a solution prepared by adding 2-mercaptoethanol or dithiothreitol to SDS-Tris-borate solution or water as a solvent by itself can be used. Water is especially preferable, from the viewpoints of improvement in peak intensity, improvement in peak separation degree, improvement in detection limit and improvement in determination accuracy.

As the water, those waters usually used in the electrophoresis of a protein, such as ultrapure water, deionized water, MILLI-Q water can be used, and MILLI-Q water is especially preferably used.

In addition, when water is used as a solution for preparing a sample, it is preferable that the protein is dissolved in water from the viewpoints of enhancement in peak intensity and improvement in detection limit.

The concentration of the protein in the sample solution is preferably from 0.05 to 2000 ng/μl, more preferably 0.1 to 2000 ng/μl, especially preferably from 0.5 to 200 ng/μl, from the viewpoint of determination accuracy.

Preferable embodiments by which the electrophoresis method of the present invention can be used include capillary electrophoresis, microchip electrophoresis, and nano-channel electrophoresis.

The capillary electrophoresis is usually carried out by filling a buffer for electrophoresis in a capillary having an inner diameter of 100 μm or less, introducing a sample into one end of the capillary, and applying a high voltage at both ends thereof to develop a test protein in the capillary. As the capillary, fumed silica capillary can be usually used, the inner wall of which may not be coated or may be coated (50% phenylmethyl polysiloxane, polyethylene glycol, polyamine and the like). Also, those without the coating treated with PEO (polyethylene oxide) or the like may be used.

In the embodiment of the capillary electrophoresis, the electrophoresis method of the present invention may be concretely carried out without heat-denaturing a protein-containing sample by a process including the steps of injecting the sample into a capillary to migrate the protein under electrophoretic electric field capable of separating proteins; and electrophoresing a protein by the electrophoretic electric field.

The step of injecting the sample into a capillary to migrate the protein under electrophoretic electric field capable of separating proteins is more specifically carried out by voltage method, pressing method or dropping method, and the magnitude of the voltage and applied pressure and the time during the method are properly determined depending upon the kinds of the apparatus, the thickness (inner diameter), the length of the capillary, and the like. Further, there can be applied the method described in WO 02/097421.

In the capillary usable in the capillary electrophoresis, the inner diameter, the outer diameter, the full length, the effective length are not particularly limited, and those of usually used sizes can be used. As to the effective length, a capillary having a short effective length can be used, from the viewpoint of enabling analysis rapidly. The effective length of the capillary as used herein refers to a distance between an inlet for injecting a sample and a detection part.

It is desired that the electrophoretic electric field in the capillary electrophoresis is preferably from 20 V/cm to 10 kV/cm, more preferably from 50 V/cm to 5 kV/cm, especially preferably from 100 V/cm to 1 kV/cm, from the viewpoints of giving an excellent separation ability and shortening the migration time.

In the microchip electrophoresis, there is used a microchip comprising a loading channel and a separating channel intersecting with the loading channel, wherein a sample reservoir is provided on one end of the loading channel, and an outlet is provided on the other end of the loading channel.

In the embodiment of the microchip electrophoresis, the electrophoresis method of the present invention may be concretely carried out without heat-denaturing a protein-containing sample by a process including the steps of supplying the sample to a sample reservoir; introducing the sample in the sample reservoir into the separating channel; and electrophoresing the sample in the separating channel.

The step of supplying the sample to a sample reservoir is more specifically accomplished by applying voltage between the sample reservoir at one end of the loading channel and the outlet at the other end thereof. The intensity of the voltage differs depending upon the apparatus. In the case of SV1100 (manufactured by Hitachi Electronics Engineering Co., Ltd.), a voltage of from 50 to 800 V, usually 300 V is applied. By applying the voltage, the sample is provided at the intersection portion of the loading channel and the separating channel. On the other hand, the method described in WO 02/097421 can be also applied.

The step of introducing the sample in the sample reservoir into the separating channel is more specifically accomplished by simultaneously carrying out the step of applying a squeezing voltage between the sample reservoir at one end of the loading channel and the outlet at the other end thereof to discharge an excess sample into the sample reservoir and into the outlet of the other end, and the step of applying a separating voltage to an outlet side of the separating channel and its opposing side. The intensity of the voltage is properly selected depending upon the apparatus. In the case of SV1100 (manufactured by Hitachi Electronics Engineering Co., Ltd.), the former is 130 V or so, and the latter is from 700 to 900 V. On the other hand, the method described in WO 02/097421 can be also applied.

The materials for the microchip include, for instance, silica glass, borosilicate glass, soda glass, polymethyl methacrylate, polycarbonate, dimethylsiloxane and the like. Among them, glass or polymethyl methacrylate is desired, from the viewpoints of little adsorption of the sample and facilitation of the chip working. In addition, there may be also used those of which inner wall is subjected to a process as in the capillary electrophoresis.

In the microchip electrophoresis, the size of the microchip is, for instance, a length of from 10 to 120 mm, a width of from 10 to 120 mm, and a thickness of from 500 to 5000 μm.

Each of the shapes of the loading channel and the separating channel in the microchip is not particularly limited. There can be also used a chip in which 3 to 96 of the above-mentioned channels are arranged on a single piece of chip, capable of simultaneously analyzing the multi-channels. The manner of arrangement of the multi-channel includes parallel, radial, circular and the like, and its shape is not particularly limited.

The width of the above-mentioned channel can be properly set depending upon the size of the microchip and its purpose of use. Specifically, it is desired that the width of the channel is 0.1 μm or more, preferably 10 μm or more, from the viewpoint of obtaining a satisfactory analytical sensitivity, and that the width is 100 μm or less, preferably 50 μm or less, from the viewpoint of obtaining a satisfactory analytical accuracy. In addition, the depth of the above-mentioned channel can be properly set depending upon the size of the microchip and its purpose of use. Specifically, it is desired that the depth is 0.1 μm or more, preferably 10 μm or more, from the viewpoint of obtaining a satisfactory analytical sensitivity, and that the depth is 100 μm or less, preferably 50 μm or less, from the viewpoint of obtaining a satisfactory analytical accuracy. Further, the length of the above-mentioned separating channel can be properly selected depending upon the size of the microchip, and the compound to be analyzed. It is desired to further extend the length of the effective length. The effective length refers to a distance between the channel intersecting portion and a detecting point of a high polymer (arranged on the separating channel). It is desired that the effective length is 0.1 mm or more, preferably 10 mm or more, from the viewpoint of obtaining a satisfactory separation ability, and that the effective length is 100 mm or less, preferably 50 mm or less, from the viewpoint of rapid separation.

In addition, the size of the above-mentioned reservoir can be properly set depending upon the volume of the sample. Specifically, it is desired that the diameter is 0.05 mm or more, preferably 3 mm or less, from the viewpoints of handling upon the introduction of the sample and the thickness of the electrode.

It is desired that the electrophoretic electric field in the microchip electrophoresis is from 20 V/cm to 50 kV/cm, preferably from 50 V/cm to 20 kV/cm, more preferably from 100 V/cm to 10 kV/cm from the viewpoints of obtaining an excellent separation ability and shortening the migration time.

The nano-channel electrophoresis refers to electrophoresis which is carried out by using a chip in which a flow path having a channel width in the nanometer size of from 1 nm to 1 μm, preferably from 10 to 500 nm, more preferably from 50 to 100 nm is formed. This embodiment includes a case where a structural member of a nano-size mentioned above is formed on the channel of a micrometer size. The shape of the structural member of a nano-size includes, but not particularly limited to, for instance, those of square, circle, triangle and the like. The setting intervals of the structural members are also not particularly limited. The nano-channel chip constituted by these structural members is used. In the same manner as the case of the capillary electrophoresis, there is included a chip capable of simultaneously analyzing the multi-channel.

The channel in the nano-channel electrophoresis can have various designs, including those in which the shape of the channel having the feature of the nanometer size has a bent curvature, those of wound shape, those of zigzag shape, or a combination of those, and the like. By having the above shape, many channels can be formed in a micro-scale. Also, by having the above shape, a large number of samples can be processed at once, so that high throughput can be accomplished. In the case where the structural member of a nano-size is formed in the channel of the micrometer size, there are some advantages that its shape can be freely varied, and that its setting intervals can be freely varied. There can be performed determination at multi-channels simultaneously.

Also in the nano-channel electrophoresis, as in the case of the microchip electrophoresis, there are included those comprising a loading channel, and a separating channel intersecting with the loading channel, wherein a sample reservoir is provided on one end of the loading channel, and an outlet is provided on the other end of the loading channel, and its shape is not particularly limited.

The materials for the nano-channel chip usable in the nano-channel electrophoresis may be the same ones as those in the microchip electrophoresis. The material includes, for instance, silica glass, borosilicate glass, soda glass, polymethyl methacrylate, polycarbonate, dimethylsiloxane, and the like.

As to the size of the nano-channel chip in the nano-channel electrophoresis, the same ones as those in the microchip electrophoresis can be applied. For instance, a length is from 10 to 120 mm, a width is from 10 to 120 mm, and a thickness is from 500 to 5000 μm. The depth of the channel, the length of the channel, the size of the reservoir and the like of the nano-channel chip are in accordance with those of the microchip.

In the electrophoresis method of a protein of the present invention, the molecular weight marker can be subjected to electrophoresis together with a protein sample. As the molecular weight marker, there can be used commercially available molecular weight markers usually used in electrophoresis of a protein, such as Agilent Technologies No. 5065-4430 having a molecular size of 6 kDa; myosin, HMW or LMW marker kit (Amersham Pharmacia Biotech), each having a molecular size of 210 kDa; or a molecular weight marker containing a protein having known molecular weight and concentration as a commercially available standard sample, or a protein purified or quantified from a biological sample. These molecular weight markers can be also used in combination.

In the electrophoresis method of a protein of the present invention, as the molecular weight marker, there can be also used two molecular weight markers for a test protein so that one molecular weight marker takes a low-molecular weight side and the other a high-molecular weight side within the determinable range. By using the molecular weight markers, more favorable adjustment in migration time and quantification can be accomplished. The molecular weight maker on the low-molecular weight side as used herein is referred to as "lower marker," and the molecular weight marker on the high-molecular weight side as used herein is referred to as "upper marker."

The lower marker includes, for instance, Agilent Technologies No. 5065-4430 having a molecular size of 6 kDa. The upper marker includes myosin having a molecular size of 210 kDa.

In the electrophoresis method of a protein of the present invention, other molecular weight marker can be used in combination with the lower marker and upper marker.

As the amount of the molecular weight marker used, there can be used in an amount generally used in electrophoresis of a protein. The concentration of the molecular weight marker in a sample solution as recommended by the manufacturer or a general protocol in accordance with the kind of the apparatus, the detection limit in the apparatus, the detection sensitivity, the determination accuracy and the like is a concentration usually usable in electrophoresis of a protein, and referred to herein as "standard concentration." For instance, in Agilent 2100 Bioanalyzer (manufactured by Agilent Technologies), a concentration of 74 ng/ml or so in a sample solution is especially preferable, from the viewpoints of test concentration, detection sensitivity and determination accuracy, and this concentration is a standard concentration.

In the electrophoresis method of a protein of the present invention, when two or more molecular weight markers are used, the detection sensitivity of the protein to be analyzed can be improved by using at least one of the molecular weight markers in a low concentration as compared to the standard concentration, a concentration of preferably from $1/30$ to $1/2$, more preferably from $1/15$ to $1/3$, especially preferably from $1/10$ to $2/7$, the standard concentration. Because the detection sensitivity exceeds the detection accuracy by expanding the scales in the low-concentration region. Further, ions in a previously prepared marker solution can be diluted by using a diluted marker. On the other hand, the lower the ionic strength during electrophoresis, the higher the sensitivity. Therefore, the sensitivity can be finally increased.

In the above-mentioned embodiments, the lower marker and/or upper marker can be used in a low concentration as compared to the standard concentration. When the lower marker is used in a low concentration as compared to the standard concentration, the concentration is preferably from $1/30$ to $1/2$, more preferably from $1/15$ to $1/3$, especially preferably from $1/10$ to $2/7$, the standard concentration. On the other hand, when the upper marker is used in a low concentration as compared to the standard concentration, the concentration is preferably from $1/20$ to $2/3$, more preferably from $1/15$ to $1/3$, especially preferably from $1/10$ to $2/7$, the standard concentration. Therefore, the detection sensitivity of the protein to be analyzed can be improved. In addition, the lower marker and/or the upper marker can be used in a lower concentration than its respective standard concentration, and further used in combination with other markers.

In addition, in the electrophoresis method of a protein of the present invention, when two or more markers are used, the detection sensitivity of the test protein can be improved by having one of the markers in a concentration substantially the same as or approximating to that of the test protein in the determination sample. Because the determination can be made accurately by setting the concentration of the molecular weight marker in a concentration substantially the same as or approximating to that of the test protein, and carrying out the determination at a position near the scale of the marker. The concentration substantially the same as or approximating to that of the test protein specifically refers to a concentration of a test protein in the determination sample of preferably from $1/10$ to 10 times, more preferably from $1/5$ to 5 times, especially preferably from $1/2$ to 2 times the concentration of the test protein in the determination sample.

In the above-mentioned embodiments, the lower marker or the upper marker can be further used in combination. In addition, the lower marker or the upper marker can be used in a concentration substantially the same as or approximating to that of the test protein. In addition, the lower marker or the upper marker can be used at a concentration substantially the same as or approximating to that of the test protein, and can be further used in combination with other molecular weight marker.

The detection method of a protein subjected to electrophoresis includes, for instance, detection by absorption by UV wavelength light, fluorescent light, laser, lamp, LED or the like, electrochemical detection, chemiluminescent detection and the like. Concretely, in the case of the protein or peptide, the protein or peptide can be detected by determining the absorption at 200 nm; reacting SYPRO Orange with the protein or peptide, exciting at 460 to 550 nm, and determining fluorescent light at 550 to 650 nm; or reacting the protein with a fluorescent marker (Agilent Technologies No. 5065-4430), exciting at 630 to 650 nm, and determining a fluorescent light at 670 to 700 nm; and electrochemical determination, chemiluminescent determination; and the like.

In the capillary electrophoresis, for instance, a device capable of emitting UV wavelength light and a detector of the UV wavelength light may be placed in the outlet of the capillary, or a device capable of emitting fluorescent wavelength and a detector of the fluorescent wavelength may be placed in the outlet.

In the microchip electrophoresis, for instance, a detector of the UV wavelength light may be placed in a detection point arranged on the separating channel, or a device capable of emitting fluorescent wavelength and a detector of the fluorescent wavelength may be placed in the detection point. Also, multi-channels can be detected simultaneously.

In the nano-channel electrophoresis, the same detector and the detection method as those of the microchip electrophoresis may be applied. Further, in the nano-channel electrophoresis, upon simultaneously detecting multi-channels, a larger number of samples can be simultaneously detected than the case of the microchip electrophoresis.

In the detection, when the identification of a protein, a peptide, an amino acid or the like is carried out, the identification can be carried out by UV absorption, the molecular weight marker, the migration time compared to the standard, analyzing mass spectrum or the like.

The present invention will be described hereinbelow more specifically by means of Examples, but the present invention is by no means limited to these Examples.

In Examples, all electrophoreses for proteins were performed with a microchip electrophoresis apparatus Agilent 2100 Bioanalyzer manufactured by Agilent Technologies, and Protein 200 Kit manufactured by the same company. The conventional method was carried out in accordance with the protocol recommended by Agilent Technologies. Specifically, the method comprises the following steps 1 to 7:

1. adding 90 µl of a denaturing buffer and 3 µl of 100 mM dithiothreitol to 3 µl of an upper marker, and mixing the mixture with Vortex for 5 seconds;
2. taking 15 µl of a stock solution for a lower marker, and mixing the stock solution with 1.0 ml of milli-Q water;
3. mixing 3 µl of a ladder solution, as well as separately 2 µl of a mixture of the denaturing buffer prepared in the above-mentioned 1. and 4 µl of a test protein sample with Vortex, and centrifuging the mixture at 1000×g for 5 seconds;
4. heating the samples of the above-mentioned 3. at 100° C. for 5 minutes;
5. after heating, allowing to cool the samples for 1 to 2 minutes;

6. adding the lower marker solution in an amount of 84 μl prepared in the above-mentioned 2. to the ladder solution and the test protein solution after heating and cooling treatments, respectively; and 7. subjecting the product prepared in the above-mentioned 6. each in an amount of 6 μl as a test sample to electrophoresis.

Here, in the electrophoresis method of a protein of the present invention, for the comparison to the conventional method, the electrophoresis of a protein was performed on the basis of the protocol recommended by Agilent Technologies with adding some modifications described in each Example.

As the lower marker, Agilent Technologies No. 5065-4430 having a molecular size of 6 kDa was used, and as the upper marker, myosin having a molecular size of 210 kDa was used.

The ladder solution as used herein refers to a standard sample of a known molecular weight for determining molecular sizes, containing each of the followings in a concentration of 74 ng/ml:

lysozyme (14.3 kDa), β-lactoglobulin (18.4 kDa), carbonic anhydrase (29.0 kDa), ovalbumin (43.0 kDa), serum albumin (68.0 kDa), phosphorylase B (97.4 kDa), myosin (210 kDa).

Example 1

FIGS. 1A-D are electropherograms for the cases where a pretreatment (heat-denaturing treatment) of a protein was carried out according to the conventional method, and thereafter microchip electrophoresis was carried out; and FIGS. 1E-M are those for the cases without the heat-denaturing treatment. As the protein, there was used 1 μg/μl bovine serum albumin (BSA) (SIGMA).

Double peaks of a migration time of 20 s or so are ascribed to the lower marker, and a single peak near a migration time of 40 s is ascribed to the upper marker. The peak of the migration time for BSA is 25 s to 30 s.

Conventional method: The results according to ordinary method (the method recommended by Agilent Technologies) are shown in FIG. 1A. On the other hand, FIG. 1B shows the results without addition of dithiothreitol in the heat-denaturing treatment. Also, FIG. 1C shows the results where deionized water (manufactured by ICN Biomedicals, Inc.) without SDS was used in place of a sample buffer (one contained in the kit of Agilent Technologies, considered as a buffer containing SDS), and FIG. 1D shows the results of a system using deionized water without addition of dithiothreitol.

As a result, the lowering in the intensity was found by using the deionized water and dithiothreitol was added to the water. On the other hand, in the case where the defined sample buffer and dithiothreitol were added without the heat-denaturing treatment, the intensity was improved from that of FIG. 1 (FIG. 1E). This improvement was not attributable to dithiothreitol (FIG. 1F).

On the other hand, in the case where a protein was dissolved in the deionized water and dithiothreitol was added to water in place of the sample buffer without the heat-denaturing treatment, a dramatic increase in intensity was shown (FIG. 1G). The same results were obtained without dithiothreitol (FIG. 1H). These results were completely the same also in the case where the upper marker was used in a 2-fold concentration (FIG. 1L). In addition, the system using the deionized water without the heat-denaturing treatment had excellent reproducibility of the intensity (FIG. 1M).

From these results, when the protein was dissolved in water, not in buffer without the heat-denaturing treatment, spectral intensity could be improved 8 to 10-folds.

Example 2

Figure 2:
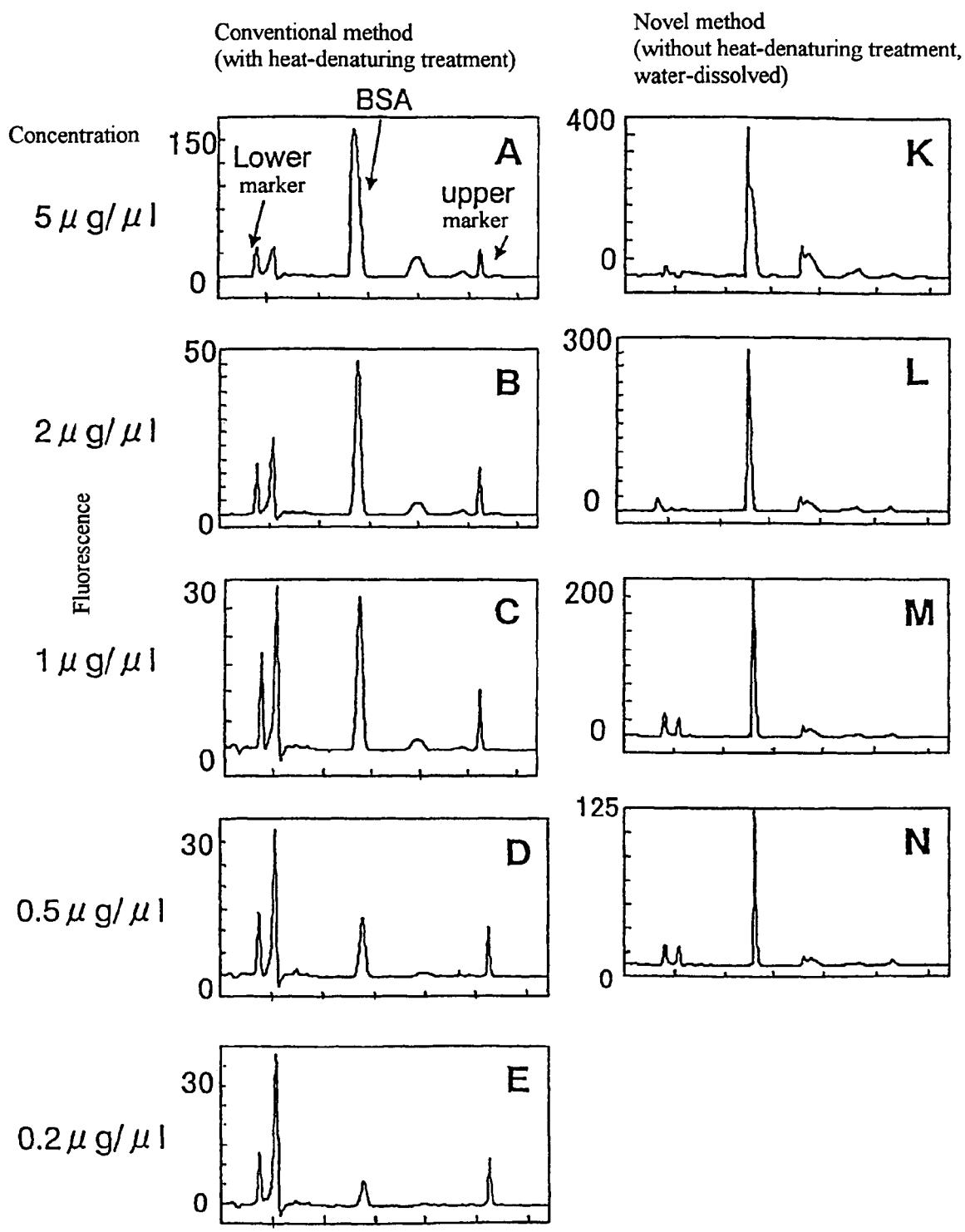
FIG. 2 shows the results for studying electrophoresis conditions in microchip electrophoresis.
Figure 2:
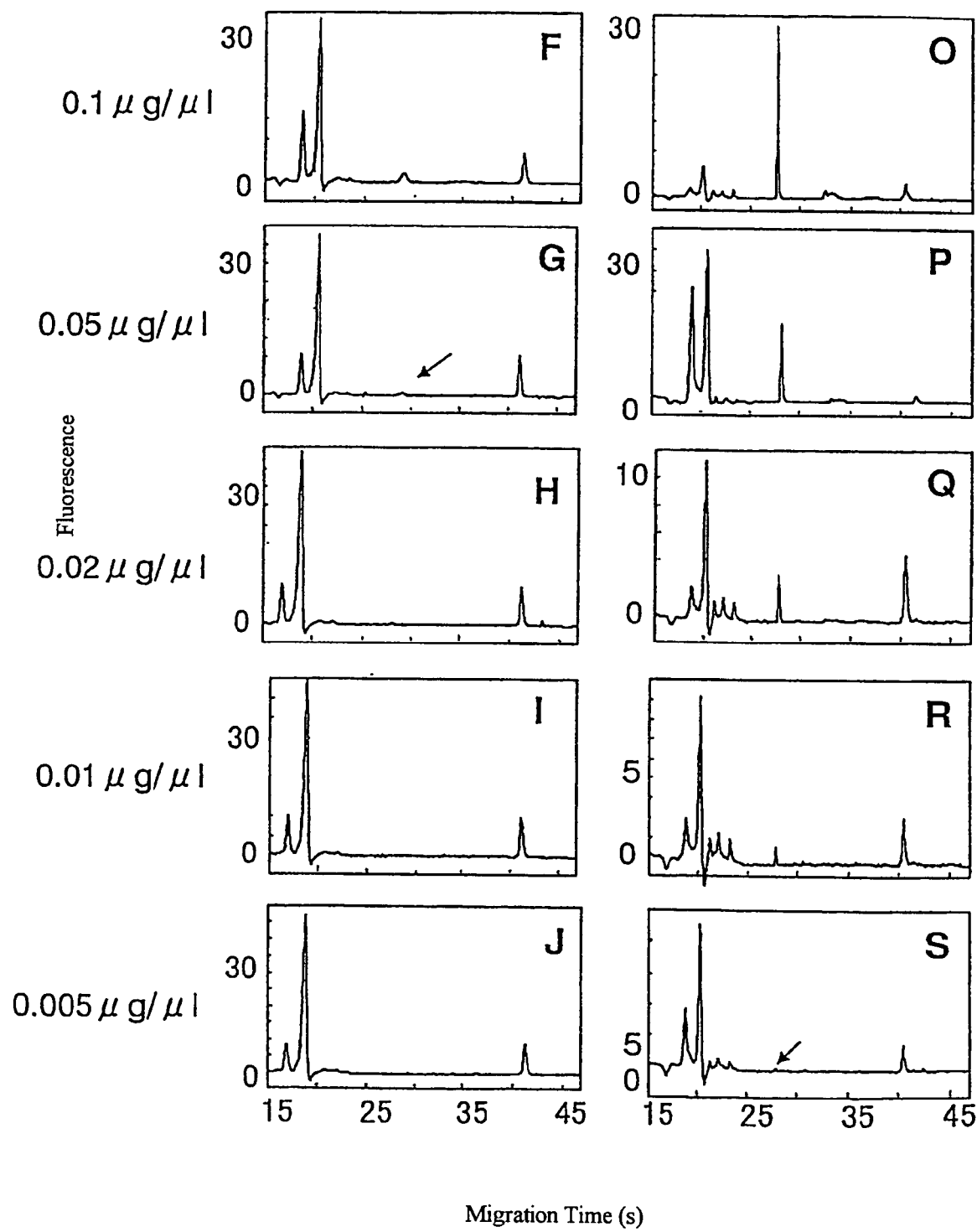

FIG. 2 shows comparison of the change in concentration with the spectral intensity between those with the heat-denaturing treatment (conventional method) and those without the treatment (described in Example 1E). FIGS. 2A-J are those with the heat-denaturing treatment, and FIGS. 2K-S are those using water but not dithiothreitol as described in Example 1 without the heat-denaturing treatment. The concentrations of a test protein BSA in FIG. 2 are: A, K: 5 μg/μl, B, L: 2 μg/μl, C, M: 1 μg/μl, D, N: 0.5 μg/μl, E: 0.2 μg/μl, F, O: 0.1 μg/μl, G, P: 0.05 μg/μl, H, Q: 0.02 μg/μl, I, R: 0.01 μg/μl, J, S: 0.005 μg/μl.

It was found from these results that the detection limit in the method of the present invention (no reaction) was 0.005 μg/μl, while that in the conventional method (with reaction) was 0.05 μg/μl, showing an increase of 10 times in sensitivity.

Example 3

Figure 3:
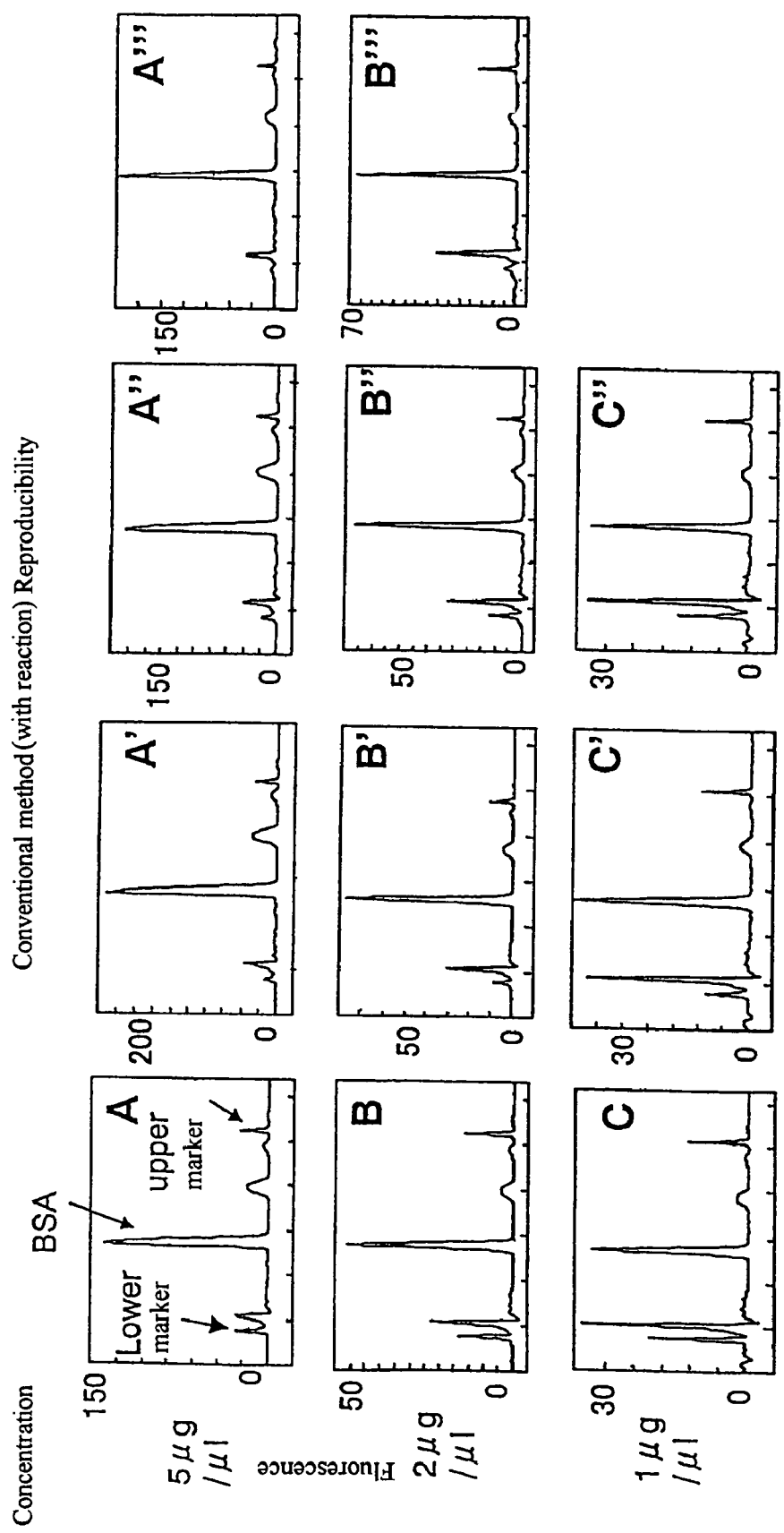
FIG. 3 shows the results for studying electrophoresis conditions in microchip electrophoresis.
Figure 3:
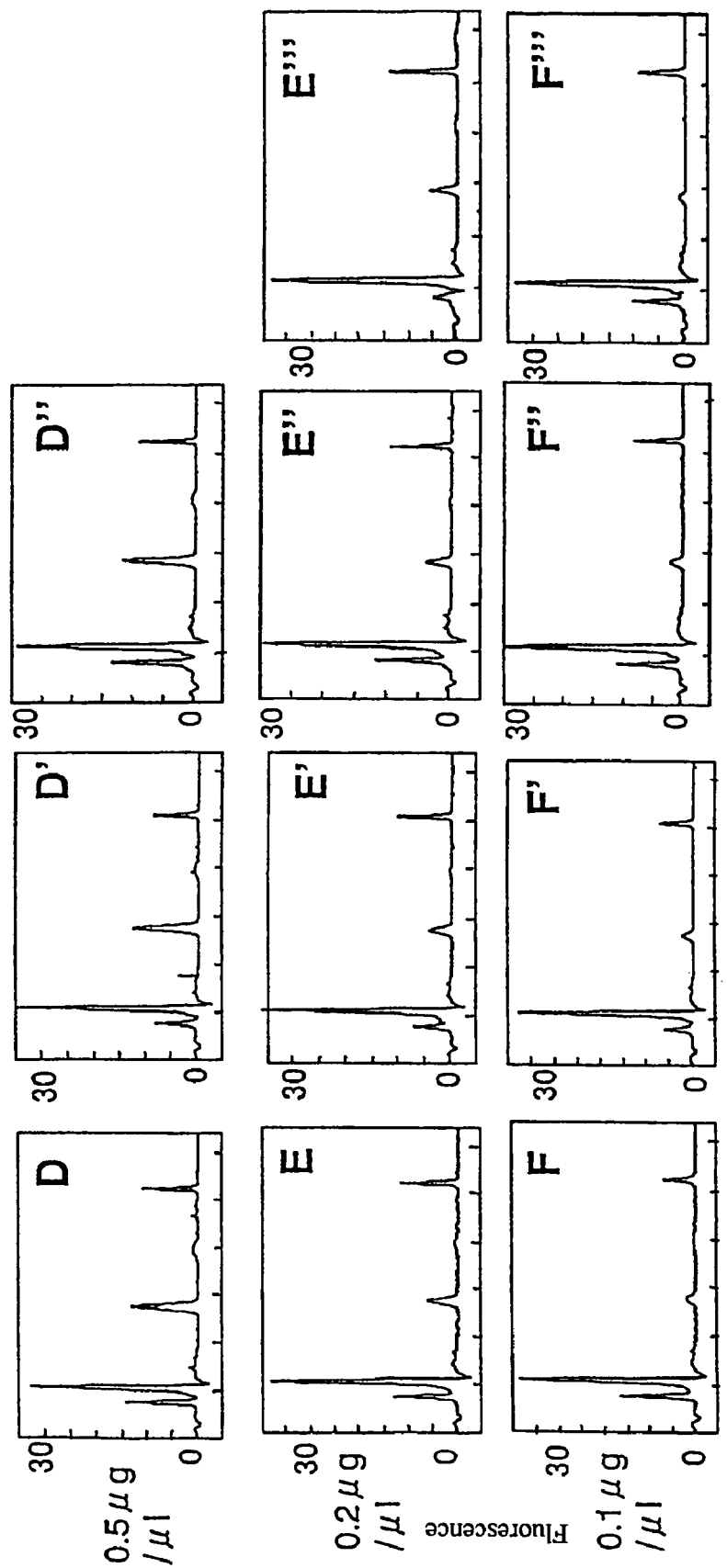
Figure 3:
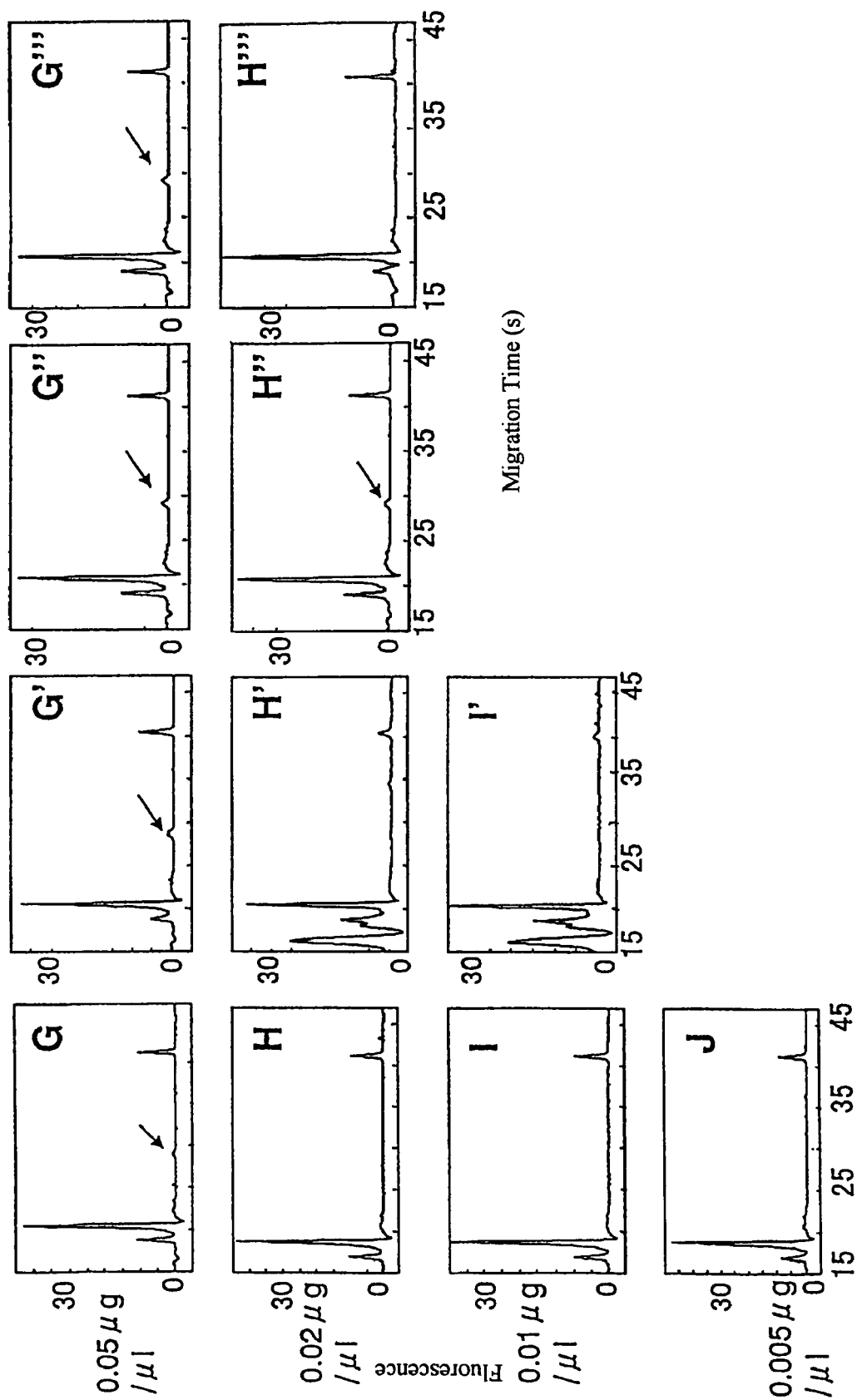

FIG. 3 shows the evaluation on reproducibility of change in concentration with the spectral intensity of Example 2 for those with heat-denaturing treatment (conventional method). The concentrations of a test protein BSA in FIG. 3 are: A-A''': 5 μg/μl, B-B''': 2 μg/μl, C-C''': 1 μg/μl, D-D''': 0.5 μg/μl, E-E''': 0.2 μg/μl, F-F''': 0.1 μg/μl, G-G''': 0.05 μg/μl, H-H''': 0.02 μg/μl I-I''': 0.01 μg/μl, J-J''': 0.005 μg/μl.

It was found from these results that the system of the conventional method (with the reaction) had a high reproducibility, and its detection limit was from 0.05-0.02 μg/μl.

Example 4

Figure 4:
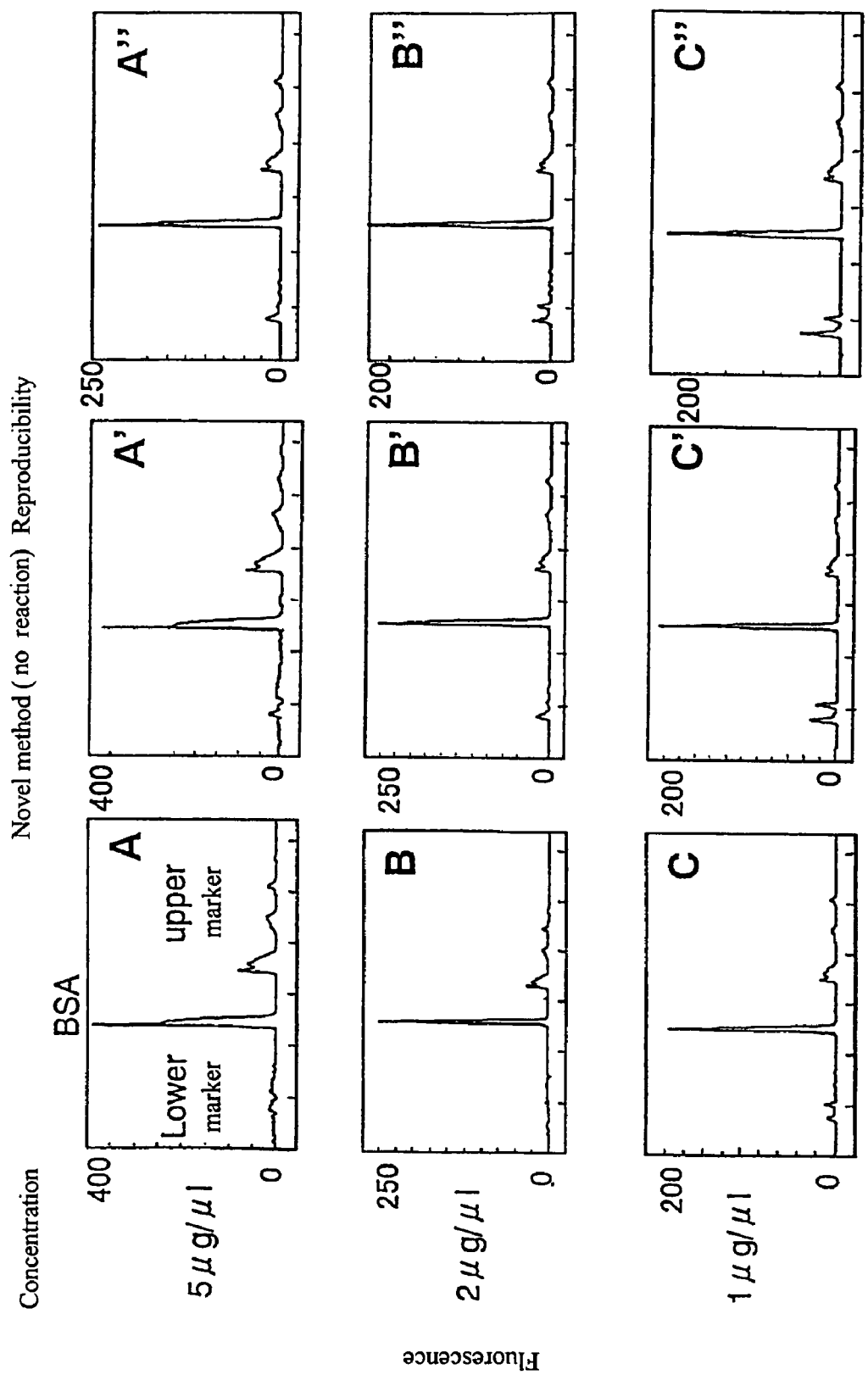
FIG. 4 shows the results for studying electrophoresis conditions in microchip electrophoresis.
Figure 4:
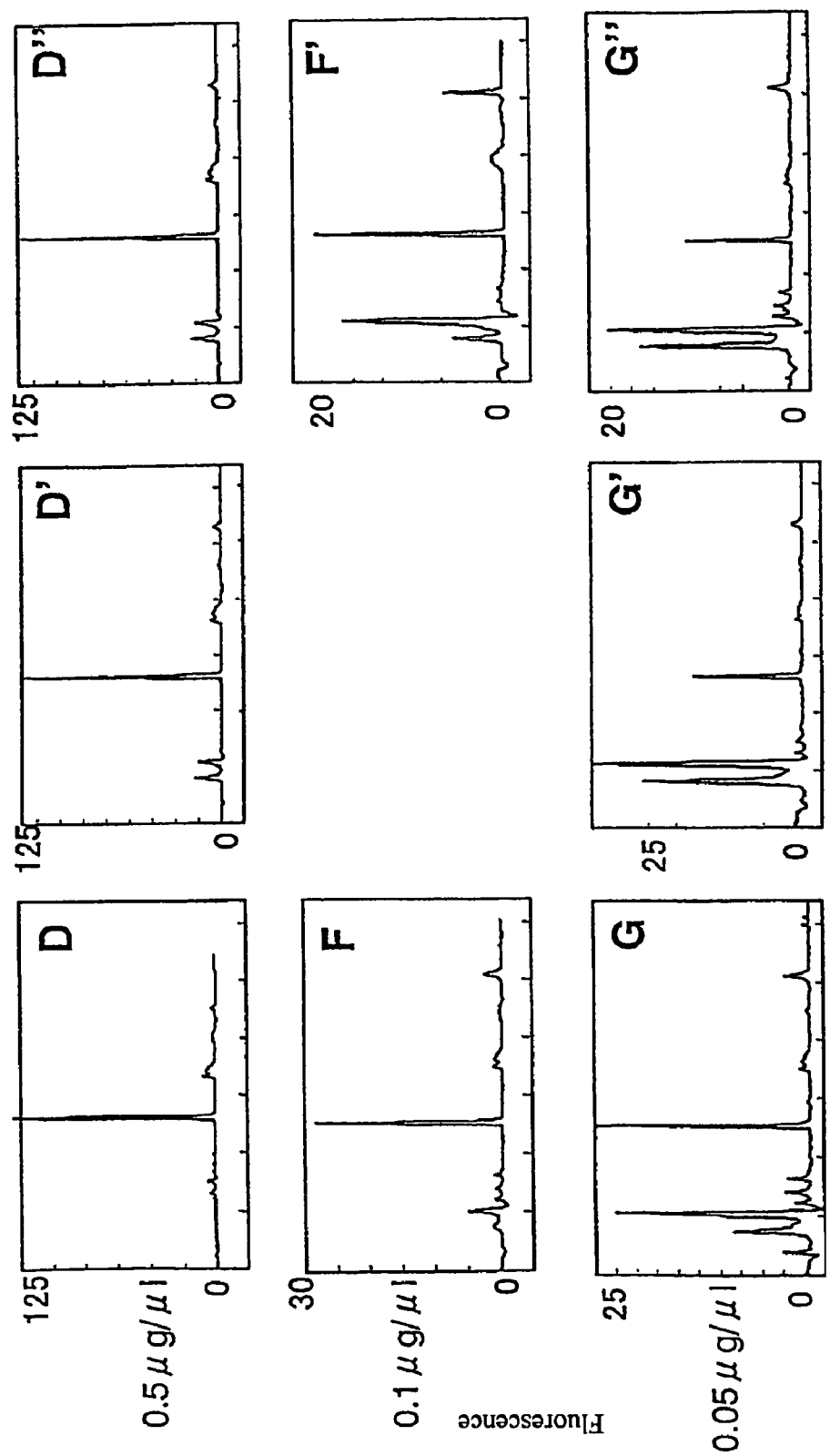
Figure 4:
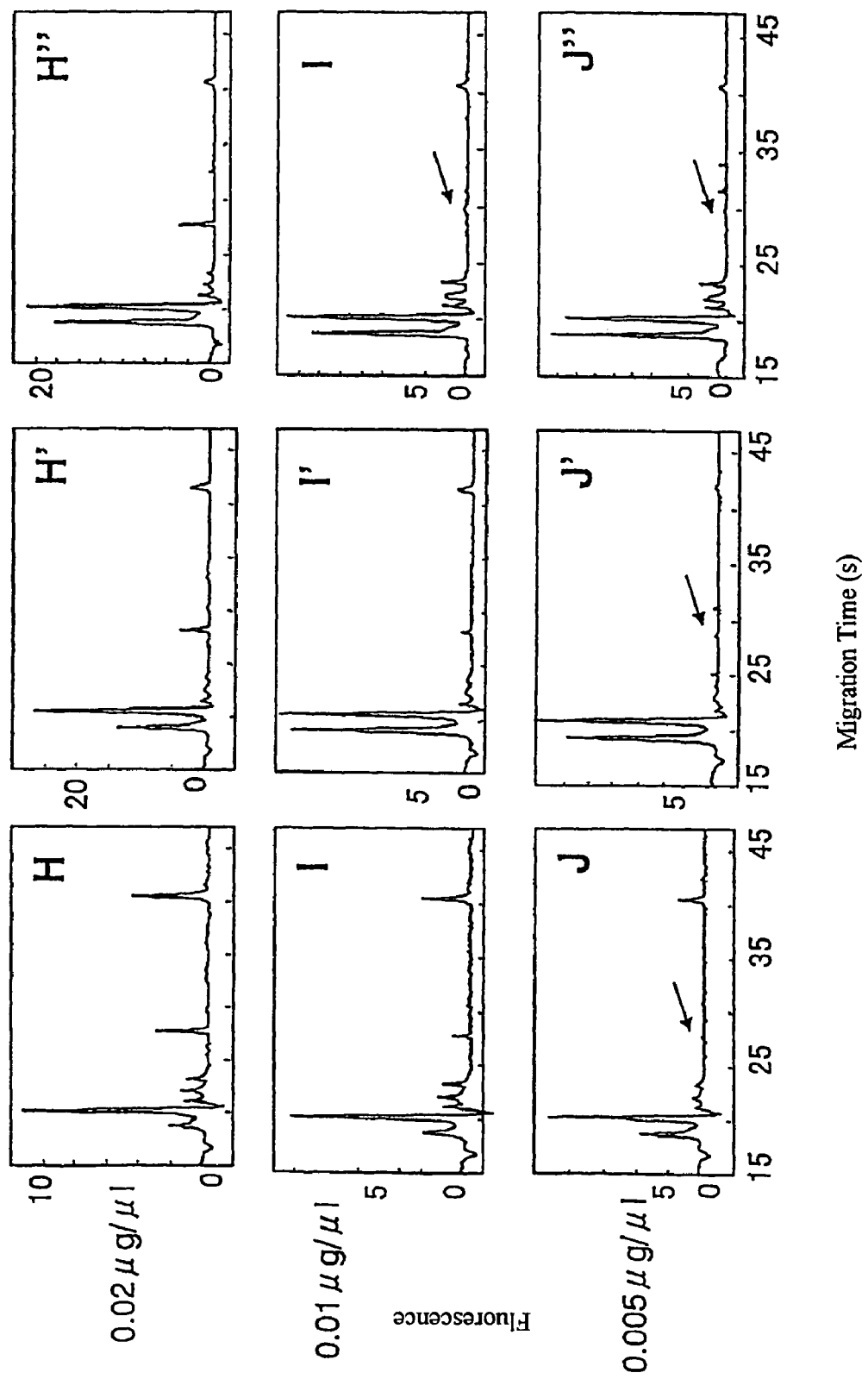

FIG. 4 shows the evaluation on reproducibility of change in concentration with the spectral intensity of Example 2 for those without the heat-denaturing treatment (one in which water described in Example 1E was added without dithiothreitol). In FIG. 4, A-A''': BSA 5 μg/μl, B-B''': 2 μg/μl, C-C''': 1 μg/μl, D-D''': 0.5 μg/μl, F-F''': 0.1 μg/μl, G-G''': 0.05 μg/μl, H-H''': 0.02 μg/μl, I, I', I'': 0.01 μg/μl, J-J''': 0.005 μg/μl.

It was found from these results that the system without the heat-denaturing treatment had a high reproducibility, and its detection limit was from 0.01-0.005 μg/μl.

Example 5

Figure 5:
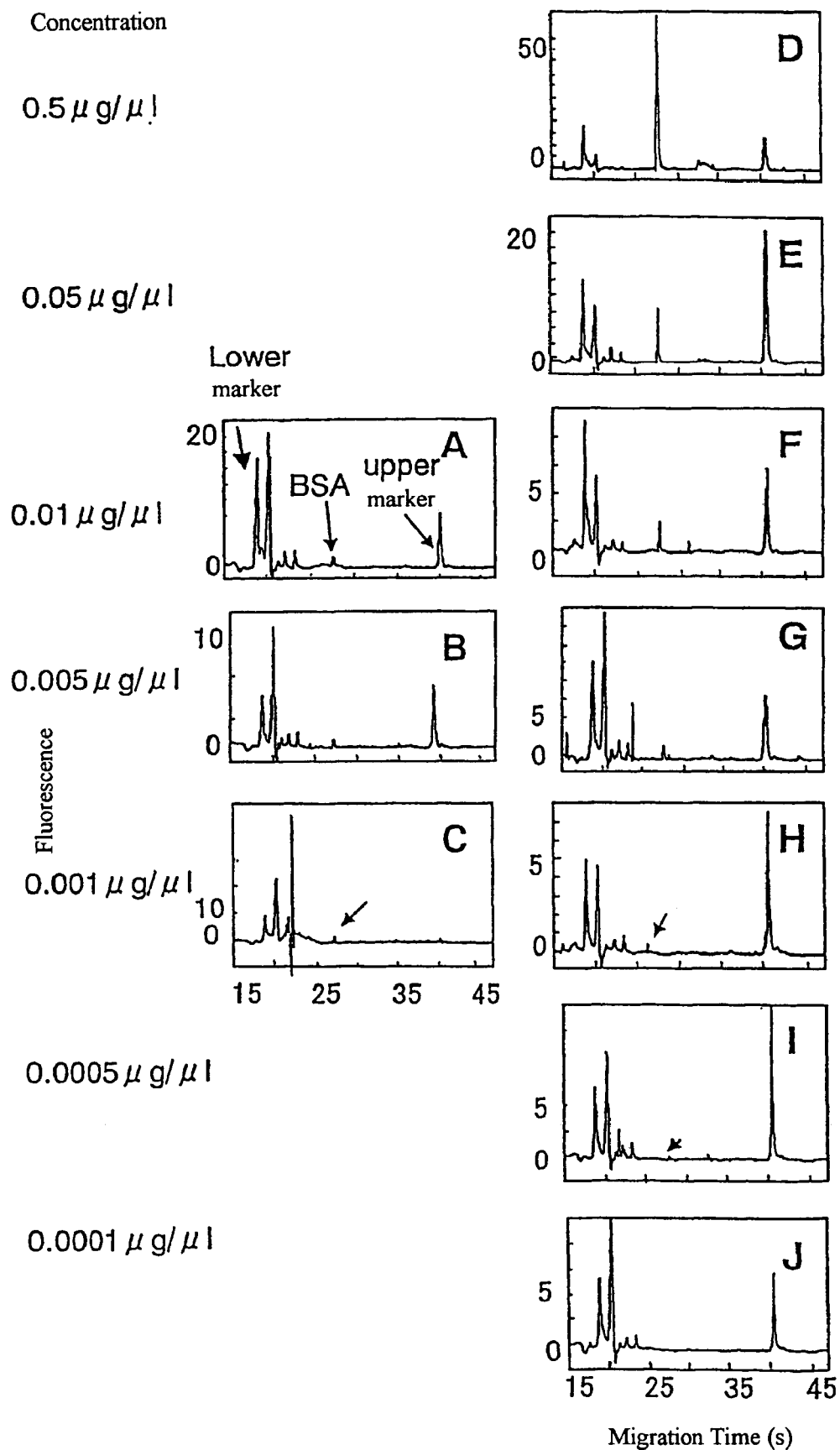
FIG. 5 shows the results for studying electrophoresis conditions in microchip electrophoresis.

FIG. 5 shows detection at a low concentration. FIG. 5A-C show the methods in which the water of the method of the present invention described in Example 1 was used without dithiothreitol, and further either one of the lower marker or the upper marker was used at a lower concentration as compared to a standard concentration. In FIG. 5, the concentrations used are: A: 0.01 μg/μl BSA, a usual lower marker concentration; B: 0.005 μg/μl BSA, ½ the conventional lower marker concentration; and C: 0.001 μg/μl BSA, ½ the conventional lower marker concentration and further ¹⁄₁₀ the conventional upper marker concentration.

FIGS. 5D-J are those in which insulin (derived from bovine spleen, SIGMA) of the same concentration as that of the test protein was further added as a lower marker to ¼ the defined concentration of the lower marker. D: 0.5 μg/μl, E: 0.05 μg/μl, F: 0.01 μg/μl, G: 0.005 μg/μl, H: 0.001 μg/μl, I: 0.0005 μg/μl, J: 0.0001 μg/μl. According to this method, the detection limit for BSA up to 0.0005 μg/μl could be determined.

Example 6

Figure 6:
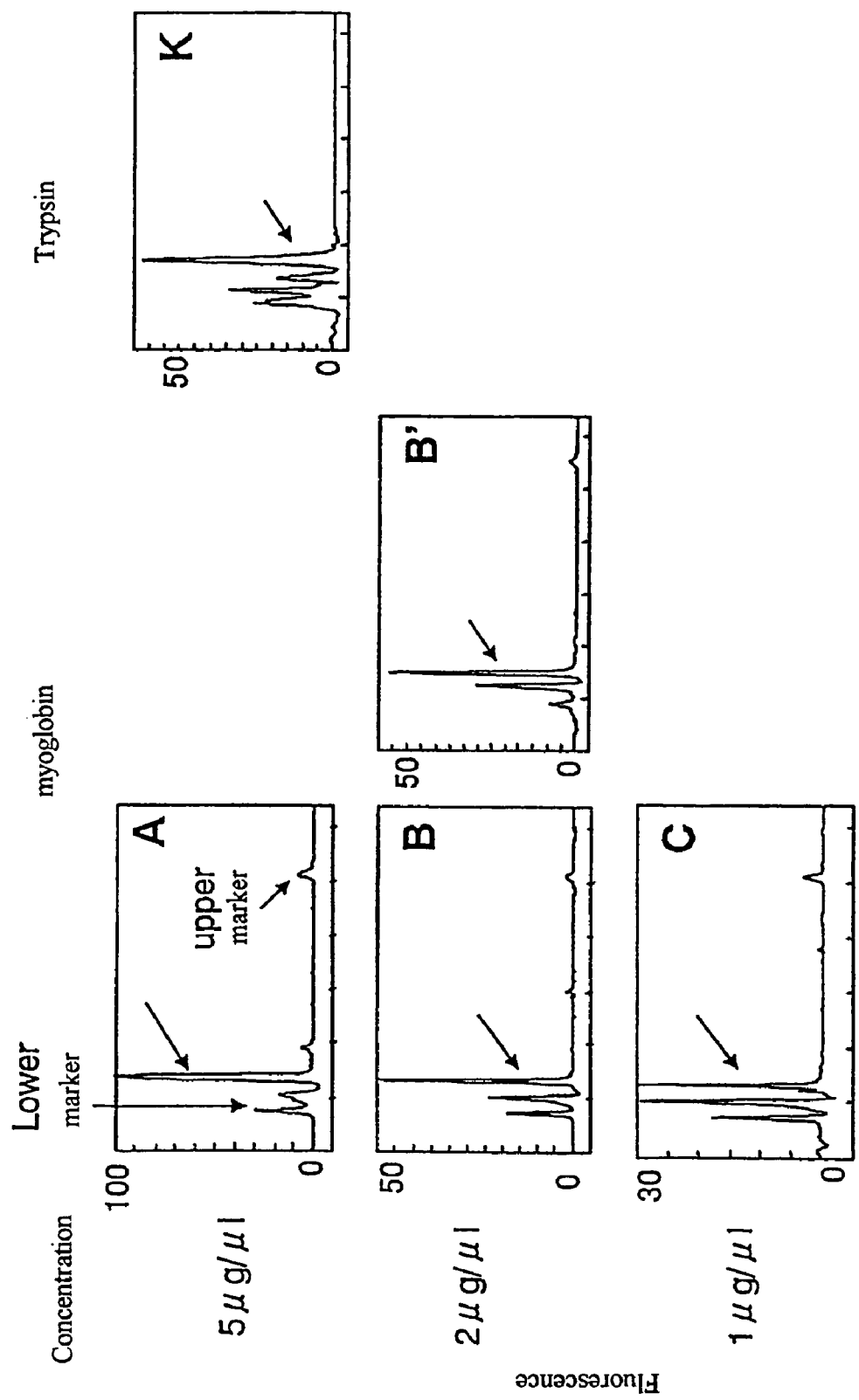
FIG. 6 shows the results for studying electrophoresis conditions in microchip electrophoresis.
Figure 6:
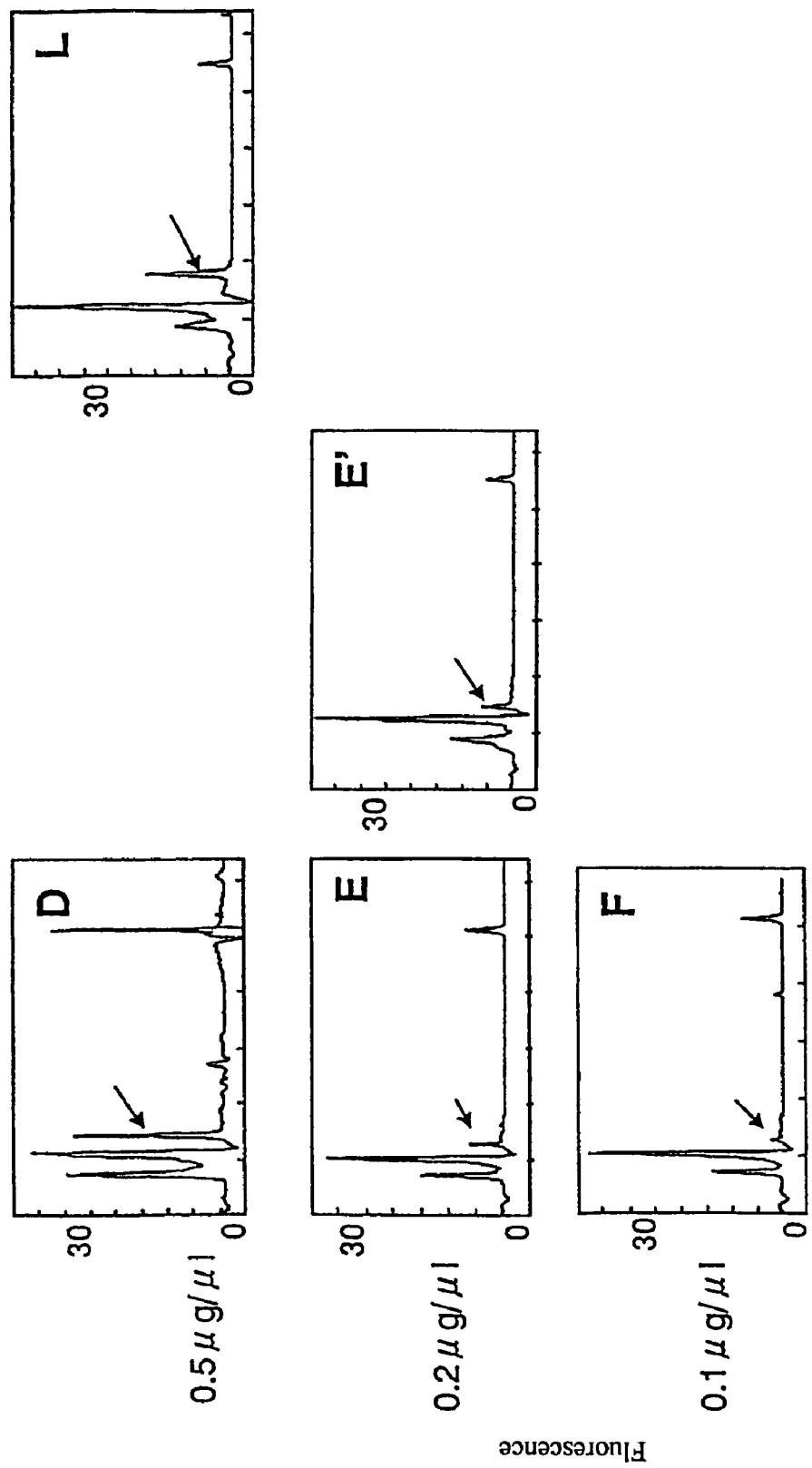
Figure 6:
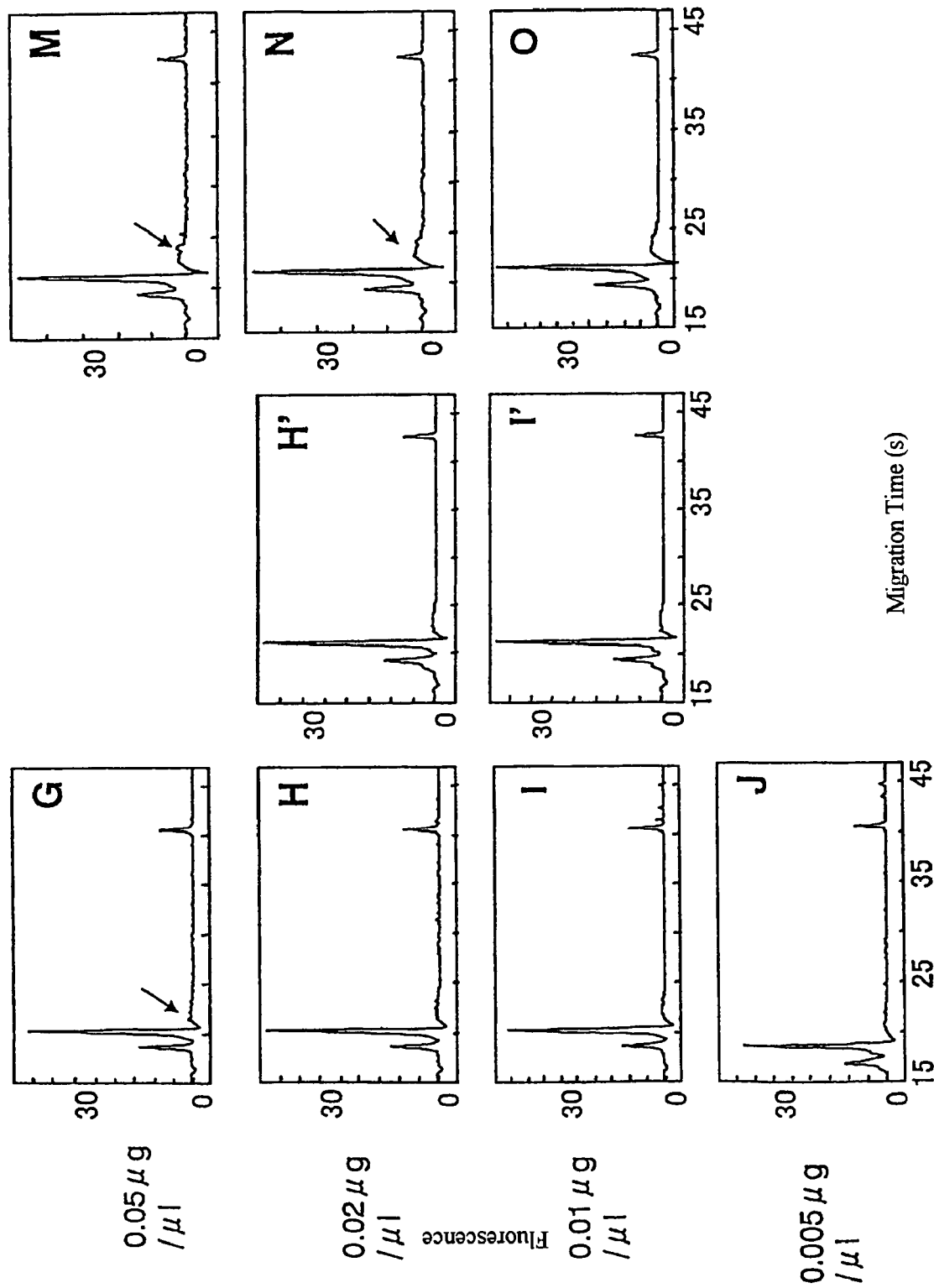

The detection limits for other proteins were examined in the same manner as in Example 5. FIGS. 6A-J are the cases for myoglobin (derived from equine skeletal muscle, SIGMA) according to the conventional method (with heat-denaturing treatment). FIGS. 6B', E', H' and I' are the cases for those similarly showing reproducibility. FIGS. 6K-O are the cases for trypsin (derived from bovine spleen, SIGMA) according to the conventional method. Each of the concentrations is: A, K: 5 µg/µl, B, B': 2 µg/µl, C: 1 µg/µl, D, L: 0.5 µg/µl, E, E': 0.2 µg/µl, F: 0.1 µg/µl, M: 0.05 µg/µl, H, H', N: 0.02 µg/µl, I, I', O: 0.01 µg/µl, J: 0.005 µg/µl. According to this method, the detection limit for both myoglobin and trypsin was 0.05-0.02 µg/µl. The results were consistent with those of BSA.

Example 7

Comparisons were made on myoglobin and BSA between the conventional method in the system with the heat-denaturing treatment and that using as a lower marker a marker having substantially the same as or an approximate amount to the test protein (here, for the sake of convenience, referred to as a variable concentration marker).

Figure 7:
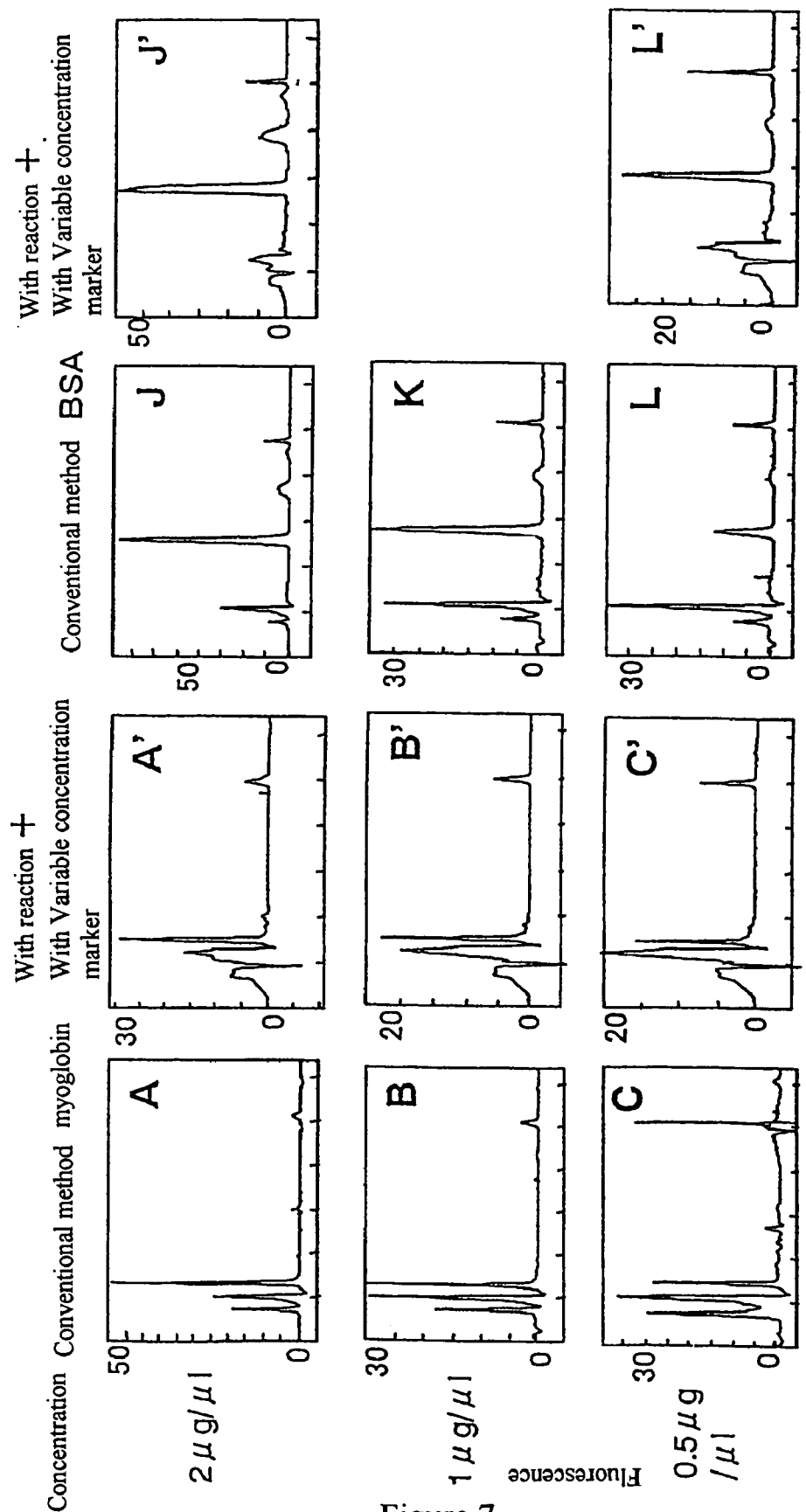
FIG. 7 shows the results for studying electrophoresis conditions in microchip electrophoresis.
Figure 7:
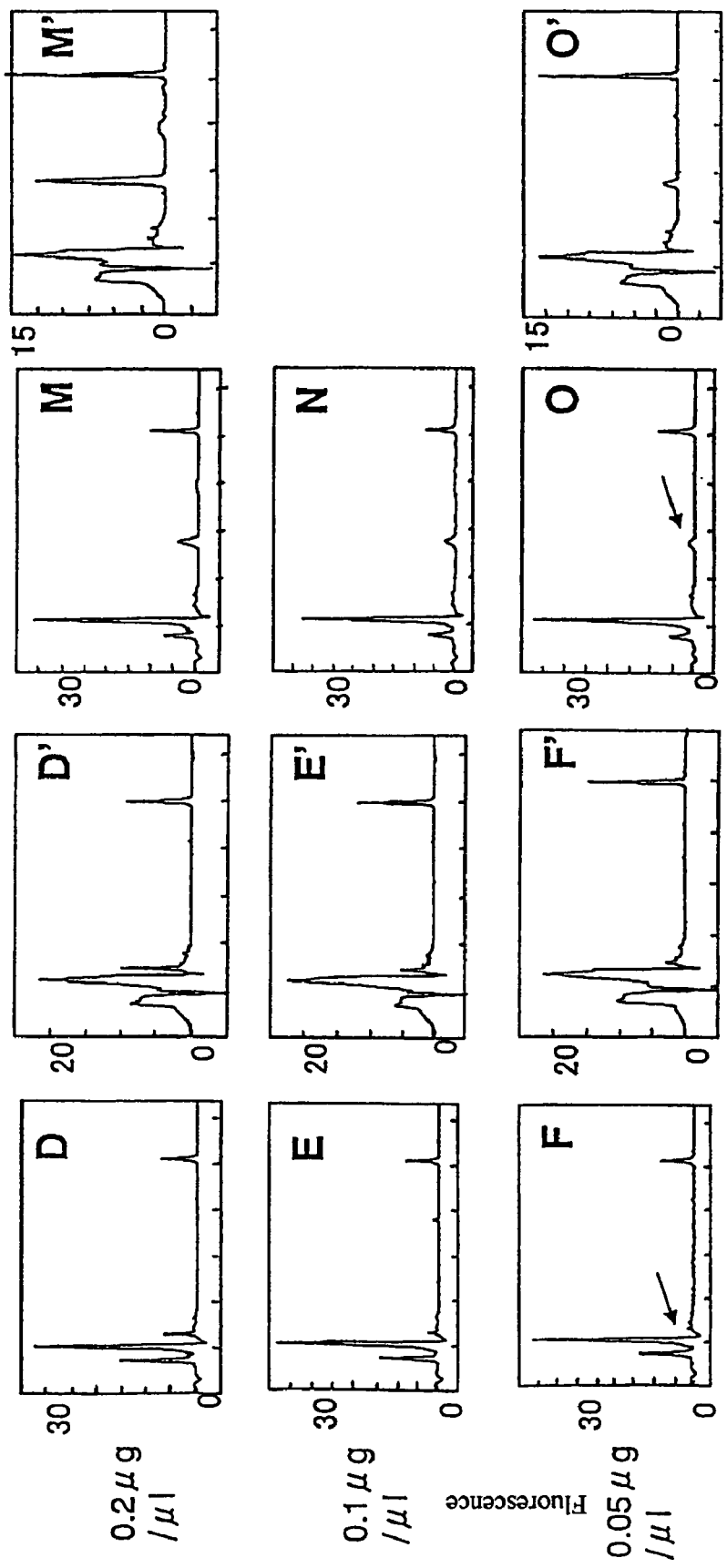
Figure 7:
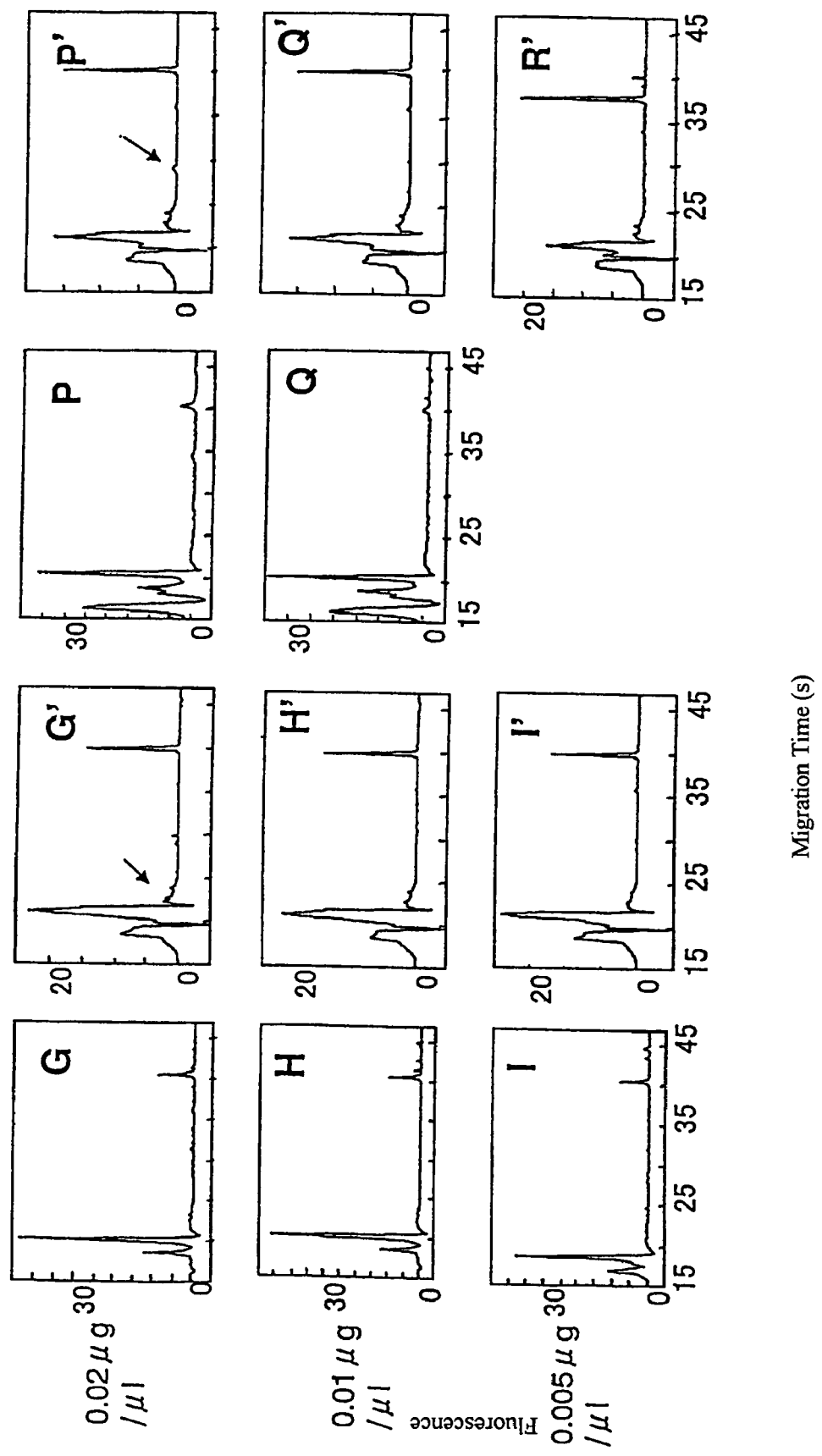

FIGS. 7A-I are the cases for myoglobin according to the conventional method (with heat-denaturing treatment). FIGS. 7A'-I' are the cases for those with the heat-denaturing treatment but using a variable concentration marker. FIGS. 7J-R are the cases for BSA according to the conventional method (with heat-denaturing treatment). FIG. 7J'-R' are the cases for those with the heat-denaturing treatment but using a variable concentration marker. In each case, insulin was used as the variable concentration marker. Each of the concentrations for the variable concentration marker is: A, A', J, J': 2 µg/µl, B, B, K: 1 µg/µl, C, C', L, L': 0.5 µg/µl, D, D', M, M': 0.2 µg/µl, E, E', N: 0.1 µg/µl, F, F', O, O': 0.05 µg/µl, G, G', P, P': 0.02 µg/µl, H, H', Q, Q': 0.01 µg/µl, I, I', R':0.005 µg/µl.

While myoglobin and BSA according to the conventional method showed a detection limit of 0.05 µg/µl, those using the variable concentration marker had a detection limit of 0.02 µg/µl, which was not a dramatic improvement as compared to the system of Example 6 without the reaction. However, it was found that in the case with the reaction, there are some effects of the variable concentration marker.

INDUSTRIAL APPLICABILITY

According to the present invention, there is provided an electrophoresis method being capable of rapidly analyzing a protein in a native state without carrying out heat-denaturing pretreatment step, and having even higher sensitivity. Therefore, the electrophoresis method of a protein of the present invention is useful for proteosome analysis and medical diagnosis.

The invention claimed is:

1. An electrophoresis method comprising:
   introducing a sample consisting essentially of a protein to be tested dissolved in water into one end of an electrophoresis channel; and
   subjecting the sample to electrophoresis in an electrophoresis buffer having a pH of 2.0 to 9.0 for size separation without a heat-denaturing treatment, wherein said electrophoresis is selected from the group consisting of capillary electrophoresis, microchip electrophoresis and nano-channel electrophoresis.

2. The electrophoresis method according to claim 1, wherein two or more molecular weight markers are subjected to electrophoresis together with the protein, wherein at least one of the markers is adjusted to a low concentration as compared to a standard concentration, wherein the standard concentration is a concentration of the molecular weight marker that is recommended by the manufacturer or a general protocol in accordance with the kind of electrophoretic apparatus, the detection limit, the detection sensitivity and determination accuracy of the electrophoretic apparatus.

3. The electrophoresis method according to claim 1, further comprising two or more molecular weight markers are subjected to electrophoresis together with the protein, wherein one of the markers is adjusted to a concentration of 1/10 to 10 times the concentration of the protein to be tested.

4. The method according to claim 1, wherein said pH is 6.8 to 8.6.

5. The method according to claim 1, wherein said method shows an increase in protein concentration during electrophoresis when compared to proteins which were heat treated.

6. The method according to claim 1, wherein said method has high reproducibility.

* * * * *